US00PP16829P2

(12) United States Plant Patent
Gossett

(10) Patent No.: US PP16,829 P2
(45) Date of Patent: Jul. 18, 2006

(54) ×*HEUCHERELLA* PLANT NAMED 'HERTN042'

(50) Latin Name: ×*Heucherella*
Varietal Denomination: HERTN042

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 102 days.

(21) Appl. No.: 11/086,075

(22) Filed: Mar. 21, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—Klarquist Sparkman, LLP

(57) ABSTRACT

A new and distinct cultivar of ×*Heucherella* plant characterized by its abundant light pink flowers, compact habit, and maple shaped leaves.

1 Drawing Sheet

Botanical name: ×*Heucherella*.
Variety denomination: 'HERTN042'.

BACKGROUND OF THE INVENTION

The present invention relates to a new and distinct intergeneric hybrid between *Heuchera* and *Tiarella*, given the cultivar name 'HERTN042'. Both genera, *Heuchera* and *Tiarella*, are of the family Saxifragaceae. This intergeneric hybrid is known as ×*Heucherella*.

The actual parents of this new variety are unknown. This new cultivar originated from crossing proprietary *Heuchera* hybrids with massed pollen from proprietary *Tiarella* hybrids. The seed from all the *Heuchera* that set was massed and sown together. This plant stood out in the field trials.

SUMMARY OF THE INVENTION

The following traits have been repeatedly observed and are determined to be the unique characteristics of 'HERTN042'. These characteristics in combination distinguish 'HERTN042' as a new and distinct cultivar:

1. Prolific bloom.
2. Light pink flower color.
3. Compact habit.
4. Maple shaped leaves with a strong white veil and red main veins.
5. Excellent vigor.

The new variety has been reproduced only by asexual propagation (division and tissue culture). Each of the progeny exhibits identical characteristics to the original plant. Asexual propagation by division and tissue culture using standard micropropagation techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
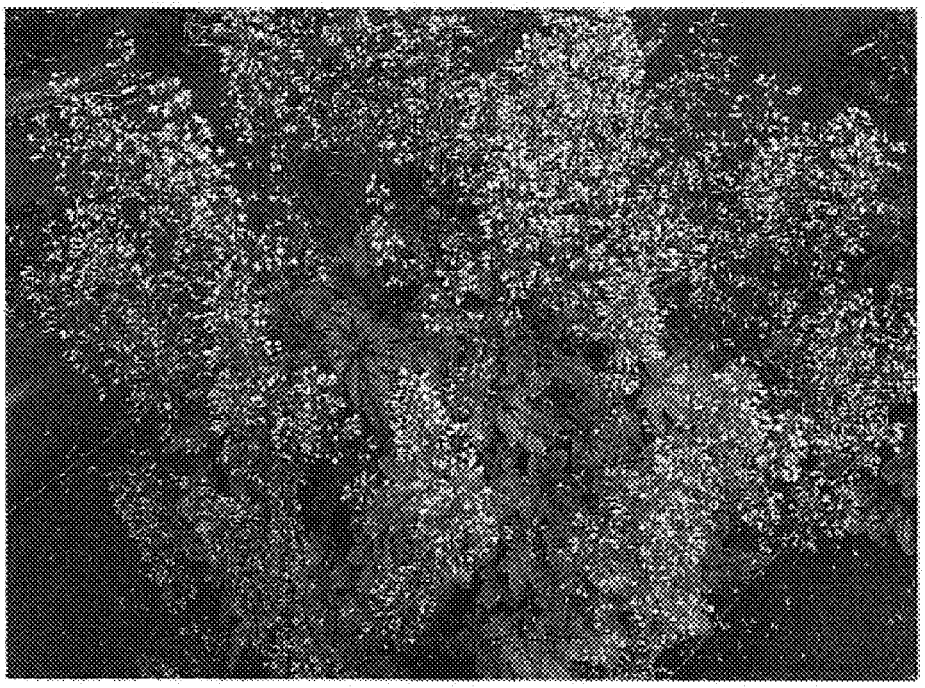
FIG. 1 shows a two-year-old plant growing in the spring in the ground in trial fields in Canby, Oreg.
Figure 2:
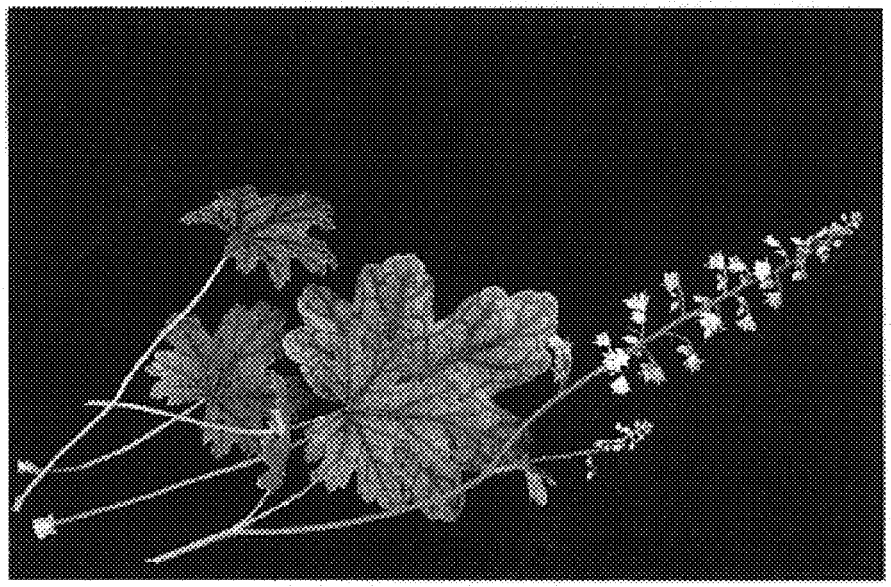
FIG. 2 shows a close-up of the leaf and flower.

The following is a detailed description of the new ×*Heucherella* hybrid based on observations of one-year-old specimens grown in a one-gallon pot in a winter cold greenhouse in Canby, Oreg. This greenhouse is kept at between 55 and 85 degrees F. in the summer months and in the winter is heated to frost free, above 32 degrees F. and vented at 55 degrees F. Light intensities are consistent with full sun in Canby, Oreg. which gets 42.8 inches of rain per year and is often cloudy. Plants were hand watered when dry. The color descriptions are all based on The Royal Horticultural Society Colour Chart.

Plant:
- *Type.*—Herbaceous perennial.
- *Form.*—Basal rosette.
- *Hardiness.*—USDA Zone 5.
- *Size.*—35 cm wide and 13 cm tall from the soil to the top of the foliage.
- *Vigor.*—Excellent.
- *Roots.*—Fibrous, freely branching, fine, and white in color. Roots develop easily from cuttings.

Leaf:
- *Type.*—Simple.
- *Arrangement.*—Rosette.
- *Shape.*—Broadly ovate to orbicular.
- *Lobing/division.*—5 to 7 lobes, cut ½ way to the leaf base, broadly oblong, with the terminal having two secondary lobes.
- *Venation.*—Palmate.
- *Margins.*—Coarsely crenate.
- *Apex.*—Mucronulate.
- *Base.*—Cordate.
- *Blade size.*—Ranges from 6 to 9 cm long and 6 to 9 cm wide.

*Surface texture.*—Sparsely pubescent, glandular on both sides.

*Petiole size.*—Ranges from 7 to 12 cm long and 1.5 mm wide.

*Petiole surface texture.*—Pubescent and with glandular hairs.

*Petiole color.*—Yellow Green 146D.

*Leaf color.*—Spring leaves — Topside — Green (Green 138A) with red veins (Red 187A) and a silver overlay (Greyed Green 189C). Bottom side — Yellow Green 147B. Summer — winter leaves — Topside — Green (Yellow Green 147A) overlaid with silver (Greyed Green 189C) and with deep brown veins (Brown 200A). Bottom side — Yellow Green 147B.

Inflorescence:

*Type.*—Thyrse.

*Number of flowers.*—Ranges from 65 to 150 per thyrse, on top 17–24 cm of peduncle.

*Number of thyrse in first spring flush.*—21.

*Peduncle.*—With 1 to 4 cauline leaves and flowering branches. Height — 42 cm. Diameter — 2 mm. Color — Yellow Green 146A to Greyed Orange 174A. Surface texture — Glandular hairs.

*Pedicel.*—Length — 0.5 to 2 mm. Surface texture — Glandular hairs. Color — Greyed Orange 174A.

*Bloom period.*—Early April to late May. Sporadic rebloom until fall in Canby, Oreg.

Flower bud:

*Size.*—5 mm deep and 2 mm wide.

*Description.*—Oblong, downfacing, with glandular hairs.

*Color.*—Light pink, Red 48D.

Flower:

*Type.*—Perfect, sepals petaloid.

*Shape.*—Campanulate.

*Size.*—9 mm wide and 6 mm deep.

*Petal count.*—5.

*Petal shape.*—Oblanceolate with a clawed base, apex acute, margins entire.

*Petal size.*—4 mm long and 1.5 mm wide.

*Petal color.*—Very light pink, Red 36D on both sides.

*Petal texture.*—Satiny.

*Calyx.*—Petaloid, divided ⅔ the way to the base, campanulate with 5 rounded lobes, apex acute, margins entire.

*Calyx size.*—9 mm wide and 5 mm deep.

*Calyx texture.*—Glandular pubescent on outside, glabrous inside.

*Calyx color.*—Outside: Red 55C and D lightening to Red 36D at base. Inside: Red 36D.

*Stamen number.*—5, sterile.

*Filaments.*—White 155D.

*Pistil.*—White 155D overall, 7 mm long.

*Fragrance.*—None.

*Lastingness.*—A thyrse blooms for about 2 weeks on the plant.

Fruit:

*Type.*—Occasional *Heuchera*-like, two-beaked capsules are formed.

*Size.*—4 to 7 mm.

*Color.*—Yellow Green 150C prior to shriveling and aborting.

Seed: None. Fertility — Sterile.

Pest and disease tolerance: No major pest or disease problems. All ×*Heucherella* may be damaged by root weevils.

COMPARISONS TO SIMILAR ×*HEUCHERELLA*

Compared to ×*Heucherella* 'Dayglow Pink' (U.S. Plant Pat. No. 12,164), this new cultivar has lighter flowers, more flowers per peduncle and over a wider area of the peduncle, and a different leaf shape, broader and more simply lobed. ×*Heucherella* 'HERTN042' also has a veiled leaf unlike 'Dayglow Pink'.

I claim:

1. A new and distinct cultivar of ×*Heucherella* plant as herein illustrated and described.

* * * * *